United States Patent

Buchanan et al.

[11] Patent Number: 5,750,811
[45] Date of Patent: May 12, 1998

[54] METHOD OF MAKING M-CHLOROBENZOTRIFLUORIDE

[75] Inventors: Robert A. Buchanan, Grand Island; Ramesh Krishnamurti, Williamsville; Habib Hichri, Snyder; David C. Johnson, Cheektowaga, all of N.Y.

[73] Assignee: Occidental Chemical Corporation, Niagara Falls, N.Y.

[21] Appl. No.: 835,183

[22] Filed: Apr. 7, 1997

[51] Int. Cl.$^6$ .................................................. C07C 17/04
[52] U.S. Cl. ................................................. 570/208
[58] Field of Search ....................................... 570/208

[56] References Cited

U.S. PATENT DOCUMENTS

| | | |
|---|---|---|
| 3,234,292 | 2/1966 | Robota . |
| 3,996,274 | 12/1976 | Jurewicz . |
| 4,186,153 | 1/1980 | Potts . |
| 4,691,066 | 9/1987 | Inoue . |

OTHER PUBLICATIONS

CA:109:1050216 abs of JP63022529, Jan. 1988.
Beilstein reg no 510215 pre section prep J Org Chem USSR 20, pp. 1993–1996, A. A. Ushakov, 1984.
Zh. Org. Khim 19(11) 2368 (1983).

*Primary Examiner*—Gary Geist
*Assistant Examiner*—Jean F. Vollano
*Attorney, Agent, or Firm*—Richard D. Fuerle

[57] ABSTRACT

Disclosed is a method of making m-chlorobenzotrifluoride. Benzotrifluoride is reacted with chlorine gas in the presence of about 0.1 to about 5 mole % (based on benzotrifluoride) of a metal chloride which can be $FeCl_3$, $SbCl_3$, or $AlCl_3$ and about 0.025 to about 5.0 mole % (based on benzotrifluoride) of a catalyst having the formula

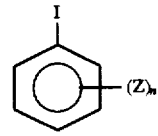

where Z is halogen, alkyl from $C_1$ to $C_6$, alkoxy from $C_1$ to $C_6$, or fluoroalkyl from $C_1$ to $C_6$, n is 0 to 5, and the molar ratio of metal chloride to cocatalyst is about 0.5 to about 4.

20 Claims, No Drawings

METHOD OF MAKING M-CHLOROBENZOTRIFLUORIDE

BACKGROUND OF THE INVENTION

This invention relates to a method of making m-chlorobenzotrifluoride by reacting benzotrifluoride with chlorine gas. In particular, it relates to the use of a catalyst system of iron chloride, antimony chloride, or aluminum chloride and an iodoaryl compound as a cocatalyst.

Meta-chlorobenzotrifluoride (MCBTF) is a valuable chemical intermediate which is useful in the preparation of pesticides and pharmaceuticals. It can be prepared by chlorinating benzotrifluoride (BTF) in the presence of a Lewis acid. This reaction produces a mixture of o-chlorobenzotrifluoride (OCBTF), MCBTF, and p-chlorobenzotrifluoride (PCBTF), as well as di-chlorobenzotrifluorides and tri-chlorobenzotrifluorides. The MCBTF is separated from the BTF, OCBTF, and di- and tri-chlorinated benzotrifluorides by distillation. Because the difference between the boiling points of MCBTF and PCBTF is small (138.1° C. and 139.2° C., respectively), PCBTF can not be easily separated by distillation from a MCBTF/PCBTF mixture. A meta/para (m/p) molar ratio greater than about 15 is generally required to produce the high purity MCBTF needed to make pesticides and pharmaceuticals. The reaction of BTF with chlorine at 21° C. and at 3° C. in the presence of ferric chloride produces MCBTF with a m/p ratio of about 10.5 and 11.5, respectively.

Various modifications to this reaction have been proposed to increase the m/p ratio. For example, U.S. Pat. No. 4,691,066 uses iodine as a cocatalyst, which improves the m/p ratio from 11 to about 14 to 18 at 20° C. However, inorganic iodides (e.g., HI, $I_2$, and ICl) are also produced. Unless these compounds are removed, severe corrosion occurs when the product is distilled. Costly and undesirable processing steps, such as aqueous extraction, are necessary to remove them. The resulting purified MCBTF typically still has an undesirable pink color due to the presence of as little as 1 ppm of these inorganic iodides.

SUMMARY OF THE INVENTION

We have discovered that the reaction of BTF with chlorine can produce a crude MCBTF product having an m/p ratio greater than about 15 if the catalyst is a mixture of ferric chloride, antimony chloride, or aluminum chloride and an iodoaryl compound. An important advantage of the method of this invention is that only low concentrations of inorganic iodides are produced, which can be easily removed. A further advantage is that, unlike many of the prior art catalysts, the cocatalysts of this invention can be re-used because they have significantly higher boiling points than MCBTF.

DESCRIPTION OF THE PREFERRED EMBODIMENTS

The method of this invention is directed at an improvement in the reaction of benzotrifluoride with chlorine, which produces MCBTF and HCl:

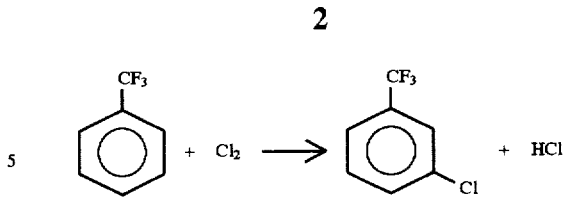

The catalyst system used in this reaction is a mixture of a metal chloride and an iodoaryl compound.

One of three metal chlorides can be used in this invention—ferric chloride ($FeCl_3$), antimony chloride ($SbCl_3$), or aluminum chloride ($AlCl_3$). The preferred metal chloride is ferric chloride as it is inexpensive and works well. The amount of metal chloride should be about 0.1 to about 5 mole % (based on BTF) as less is ineffective and more is unnecessary. Preferably, the amount of metal chloride should be about 0.2 to about 0.6 mole %. The metal chloride is a solid which dissolves in the BTF in the presence of chlorine gas.

The cocatalyst is an iodoaryl compound having the general formula

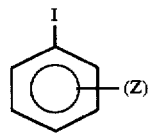

where Z is halogen, alkyl from $C_1$ to $C_6$, alkoxy from $C_1$ to $C_6$, or fluoroalkyl from $C_1$ to $C_6$ and n is 0 to 5. Preferably, Z is chlorine, fluorine, or trifluoromethyl as those compounds are more effective cocatalysts and n is preferably 0 or 1 because those cocatalysts are usually less expensive. The amount of cocatalyst should be about 0.025 to about 5.0 mole % (based on BTF) as less is ineffective and more is unnecessary. The preferred amount of cocatalyst should be about 0.05 to about 1.2 mole %. In addition, the molar ratio of metal chloride to iodoaryl cocatalyst should be about 0.5 to about 4 so that an excess of the metal chloride or the cocatalyst is not present. Preferably, the molar ratio of metal chloride to cocatalyst should be about 1 to about 4. Examples of suitable cocatalysts include iodobenzene, p-diiodobenzene, o-fluoroiodobenzene, m-fluoroiodobenzene, p-fluoroiodobenzene, o-methoxyiodobenzene, m-methoxyiodobenzene, p-methoxyiodobenzene, 2,4-diiodo-1-methoxybenzene, 2,4,6-triiodo-1-methoxybenzene, o-iodobenzotrifluoride, m-iodobenzotrifluoride, and p-iodobenzotrifluoride. The preferred cocatalyst is m-iodobenzotrifluoride as it has been found to produce the highest m/p ratio, but iodobenzene is also very effective.

While the components of the reaction can be mixed together in any order, it is preferable to mix together the BTF, metal chloride, and cocatalyst, then sparge chlorine gas into the resulting solution. The consumption of the chlorine gas as it reacts can be followed by gas chromatograph (GC) to determine the completion of the reaction. The amount of chlorine gas used should be about 0.7 to about 1.1 equivalents as too much chlorine gas results in the formation of dichlorinated compound and, if insufficient chlorine gas is used, BTF conversion is low, which is not cost effective. The reaction can be performed at about −10° to about 40° C. Lower temperatures require a longer reaction time and higher temperatures may result in the formation of more PCBTF. The preferred reaction temperature is between 0° and 20° C. The reaction is normally complete in about 1 to about 20 hours.

After the reaction has been completed, the desired product, MCBTF, must be separated and recovered from the crude product. MCBTF can be isolated from the crude reaction product by standard procedures well known to those skilled in the art. For example, the crude product can be: (1) purged with nitrogen to remove the hydrogen chloride formed in the reaction; (2) filtered to remove particulate $FeCl_3$; (3) extracted with aqueous media to remove dissolved $FeCl_3$; (4) dried to remove water; or (5) fractionally distilled to separate MCBTF and PCBTF from OCBTF and to recover unreacted BTF. The standard work-up procedure is disadvantageous because aqueous extraction introduces water which makes the organic layer corrosive and in turn leads to corrosion of the fractional distillation column. The preferred work-up is: (1) nitrogen purge to remove HCl; (2) flash distillation at atmospheric or reduced pressure to remove $FeCl_3$; (3) passing the distillate through carbon, alumina, magnesium oxide, or copper to remove trace inorganic iodides; and (4) fractional distillation to separate MCBTF and PCBTF from OCBTF and to recover unreacted BTF. The preferred method avoids corrosion problems introduced by water, efficiently removes inorganic iodides from the process, and permits re-use of the $FeCl_3$ catalyst and the aryl iodide cocatalyst.

The following examples further illustrate this invention.

EXAMPLE 1

A dry, 50 ml glass reactor equipped with a gas inlet tube, condenser, and thermometer was charged with 0.391 g anhydrous $FeCl_3$ (0.0024 moles, 0.68 mole %), BTF (0.35 moles) and 0.327 g iodobenzene (0.0016 moles, 0.45 mole %). The reaction mixture was stirred with a magnetic stirrer. Chlorine gas was added via the gas inlet tube at a rate of 6.5 g/hr for 2 hours. The internal pot temperature was maintained at 21° C. by external cooling. Samples were withdrawn periodically to monitor the reaction products by GC analysis.

EXAMPLES 2 TO 6

The conditions of Example 1 were duplicated except that iodobenzene was replaced by different iodoaryl compounds.

COMPARATIVE EXAMPLE 1

The conditions of Example 1 were duplicated except that iodobenzene was replaced with molecular iodine (molar ratio based on iodine atoms).

COMPARATIVE EXAMPLE 2

The conditions of Example 1 were duplicated except that no cocatalyst was added. The results of Examples 1 to 6 and Comparative Examples 1 and 2 are given in Table 1. In all these Examples, the temperature was 21° C. and 0.30 equivalents of chlorine were added.

COMPARATIVE EXAMPLE 3

The conditions of Example 1 were duplicated except that $FeCl_3$ was omitted. No chlorination of BTF was observed.

EXAMPLE 7

A dry, 5 liter glass reactor equipped with a gas inlet tube, condenser, and thermometer was charged with 36.02 g anhydrous $FeCl_3$ (0.222 moles, 0.68 mole %), 4,800 g BTF (32.9 moles), and 22.86 g iodobenzene (0.112 moles, 0.34 mole %). The reaction mixture was stirred by a mechanical stirrer. Chlorine gas was added via the gas inlet tube at a rate of 190 g/hr for 10 hours. The internal pot temperature was maintained at 5° C. by external cooling. Samples were withdrawn periodically to monitor the reaction products by GC analysis. The results are summarized in Table 2.

COMPARATIVE EXAMPLE 4

A dry, 5 liter glass reaction equipped with a gas inlet tube, condenser, and thermometer was charged with 21.70 g anhydrous $FeCl_3$ (0.133 moles, 0.40 mole %), 4,800 g BTF (32.9 moles), and 12.53 g iodine (0.049 moles, 0.15 mole %). The reaction mixture was stirred with a mechanical stirrer. Chlorine gas was added via the gas inlet tube at a rate of 250 g/hr for 9 hours. The internal pot temperature was maintained at 20° C. by external cooling. Samples were withdrawn periodically to monitor the reaction products by GC analysis. The results are summarized in Table 2.

EXAMPLES 8 TO 15

The conditions of Example 1 were duplicated except that changes in the reaction temperature, type of iodoaryl compound, amount of iodoaryl compound, and amount of $FeCl_3$ were made as indicated in Table 3.

TABLE 1

| Example | Reaction Temp. (°C.) | Cocatalyst | Cocat (mole %) | $FeCl_3$ (mole %) | $FeCl_3$/ cocat | $Cl_2$ Eff.* | m/p @ 0.30 Eq. $Cl_2$ |
|---|---|---|---|---|---|---|---|
| Ex. 1 | 21° C. | iodobenzene | 0.45 | 0.68 | 1.5 | 98% | 16.7 |
| Ex. 2 | 21° C. | m-iodobenzotrifluoride | 0.45 | 0.68 | 1.5 | 99% | 18.5 |
| Ex. 3 | 21° C. | o-iodobenzotrifluoride | 0.45 | 0.68 | 1.5 | 100% | 17.3 |
| Ex. 4 | 21° C. | p-iodo-anisole | 0.45 | 0.68 | 1.5 | 91% | 16.1 |
| Ex. 5 | 21° C. | 4-chloro-3-iodobenzotrifluoride | 0.45 | 0.68 | 1.5 | 100% | 15.3 |
| Ex. 6 | 21° C. | iodopentafluorbenzene | 0.45 | 0.68 | 1.5 | 88% | 10.9 |
| Comp Ex. 1 | 21° C. | iodine | 0.45 | 0.68 | 1.5 | 98% | 15.3 |
| Comp. Ex. 2 | 21° C. | none | 0.76 | na | na | na | 10.5 |

*Efficiency

TABLE 2

| Example | Reaction Temp. (°C.) | Cocatalyst | Cocat. (mole %) | FeCl₃ (mole %) | Iodine as "inorganic iodide" | Iodine as "organic iodide" | m/p @ 0.70 Eq. Cl₂ |
|---|---|---|---|---|---|---|---|
| Ex. 7 | 5 | Iodobenzene | 0.34 | 0.68 | <0.2% | >99.8% | 19.9 |
| Comp. Ex. 4 | 20 | Iodine | 0.15 | 0.40 | 72% | 28% | 17.0 |

TABLE 3

| Example | Reaction Temp. (°C.) | Cocatalyat | Cocat (mole %) | FeCl₃ (mole %) | ratio FeCl₃/ cocat | m/p @ 0.30 Eq. Cl₂ | m/p @ 0.70 Eq. Cl₂ |
|---|---|---|---|---|---|---|---|
| Ex. 8 | 3 | m-iodobenzotrifluoride | 0.62 | 0.68 | 1.1 | 21.7 | 21.0 |
| Ex. 9 | 3 | iodobenzene | 0.72 | 0.90 | 1.3 | 20.6 | 19.9 |
| Ex. 10 | 3 | iodobenzene | 0.65 | 0.68 | 1.0 | 20.5 | 19.8 |
| Ex. 11 | 3 | iodine | 0.15 | 0.35 | 1.2 | 19.8 | 20.1 |
| Ex. 12 | 3 | iodobenzene | 1.43 | 0.66 | 0.5 | 19.0 | 19.3 |
| Ex. 13 | 3 | p-iodo-anisole | 0.22 | 0.25 | 1.1 | 18.8 | na |
| Ex. 14 | 21 | o-iodofluorobenzene | 1.38 | 0.71 | 0.5 | 18.0 | 16.1 |
| Ex. 15 | 34 | m-iodobenzotrifluoride | 0.62 | 0.68 | 1.1 | 16.5 | 16.0 |
| Ex. 16 | 16 | iodobenzene | 0.45 | 0.68 | 1.5 | 17.7 | 17.3 |

We claim:

1. A method of making m-chlorobenzotrifluoride comprising reacting benzotrifluoride with chlorine gas in the presence of about 0.1 to about 5 mole % (based on benzotrifluoride) of a metal chloride selected from the group consisting of $FeCl_3$, $SbCl_3$, $AlCl_3$, and mixtures thereof and about 0.025 to about 5.0 mole % (based on benzotrifluoride) of a cocatalyst having the formula

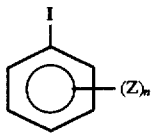

where Z is halogen, alkyl from $C_1$ to $C_6$, alkoxy from $C_1$ to $C_6$, or fluoroalkyl from $C_1$ to $C_6$, n is 0 to 5, and the molar ratio of metal chloride to cocatalyst is about 0.5 to about 4.

2. A method according to claim 1 wherein said metal chloride is $FeCl_3$.

3. A method according to claim 1 wherein Z is Cl, F, or $CF_3$.

4. A method according to claim 1 wherein n is 0 or 1.

5. A method according to claim 1 wherein said cocatalyst is iodobenzene.

6. A method according to claim 1 wherein the amount of said metal chloride is about 0.2 to about 0.6 mole % (based on benzotrifluoride).

7. A method according to claim 1 wherein the amount of said cocatalyst is about 0.05 to about 1.2 mole % (based on benzotrifluoride).

8. A method according to claim 1 wherein the molar ratio of metal chloride to cocatalyst is about 1 to about 4.

9. A method according to claim 1 wherein the amount of said chlorine gas is about 0.7 to about 1.1 equivalents.

10. A method according to claim 1 wherein the reaction temperature is about −10° to about 40° C.

11. A method according to claim 1 including the additional last steps of purging the product of said reaction with nitrogen to remove HCl, flash distilling at atmospheric or reduced pressure to remove $FeCl_3$, passing the distillate through carbon, alumina, magnesium oxide, or copper to remove trace inorganic iodides, and distilling to separate m-chlorobenzotrifluoride and p-chlorobenzotrifluoride from o-chlorobenzotrifluoride and recover unreacted benzotrifluoride.

12. A method according to claim 1 wherein said cocatalyst is m-iodobenzotrifluoride.

13. A method according to claim 1 where said cocatalyst is recovered and re-used.

14. A method of making m-chlorobenzotrifluoride comprising passing chlorine gas through benzotrifluoride in the presence of (1) about 0.2 to about 0.6 mole % (based on benzotrifluoride) of ferric chloride; and (2) about 0.05 to about 1.2 mole % (based on benzotrifluoride) of a cocatalyst having the formula

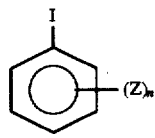

where Z is F or $CF_3$, n is 0 or 1, and the molar ratio of ferric chloride to cocatalyst is about 1 to about 2.

15. A method according to claim 14 wherein the reaction temperature is about −10° to about 40° C.

16. A method according to claim 14 including the additional last steps of purging the product of said reaction with nitrogen to remove HCl, flash distilling at atmospheric or reduced pressure to remove $FeCl_3$, passing the distillate through carbon, alumina, magnesium oxide, or copper to remove trace inorganic iodides, and distilling to separate m-chlorobenzotrifluoride and p-chlorobenzotrifluoride from o-chlorobenzotrifluoride and recover unreacted benzotrifluoride.

17. A method according to claim 14 wherein the amount of said chlorine gas is about 0.7 to about 1.1 equivalents.

18. A method of making m-chlorobenzotrifluoride comprising
  (A) forming a composition of
    (1) benzotrifluoride;
    (2) about 0.2 to about 0.6 mole % (based on benzotrifluoride) of ferric chloride; and
    (3) about 0.05 to about 1.2 mole % (based on benzotrifluoride) of m-iodobenzotrifluoride, where the molar ratio of ferric chloride to m-iodobenzotrifluoride is about 1 to about 4 and the temperature of said composition is about $-10°$ to about $40°$ C.;
  (B) reacting about 0.7 to about 1.1 equivalents of chlorine gas with said benzotrifluoride;
  (C) removing solids from said composition; and
  (D) removing said m-chlorobenzotrifluoride by distillation.

19. A method according to claim 18 wherein said solids are removed by passing said composition through carbon, alumina, magnesium oxide, or copper.

20. A method according to claim 18 wherein said composition is passed through activated carbon, alumina, magnesium oxide, or copper prior to said distillation.

* * * * *